United States Patent [19]

Kamei et al.

[11] Patent Number: 4,740,505

[45] Date of Patent: Apr. 26, 1988

[54] PYRIDAZINYLOXY (OR THIO) PHENYL PHOSPHATES

[75] Inventors: Kazuo Kamei; Nobuo Matsumoto, both of Tokyo; Yasuo Sato, Kyoto, all of Japan

[73] Assignees: Takeda Chemical Industries, Ltd.; Nippon Chemical Industrial Co., Ltd., both of Tokyo, Japan

[21] Appl. No.: 829,996

[22] Filed: Feb. 18, 1986

[30] Foreign Application Priority Data

Feb. 15, 1985 [JP] Japan .................................. 60-28801

[51] Int. Cl.⁴ .......................... A01N 57/16; C07F 9/15
[52] U.S. Cl. ...................................... 514/85; 544/232; 544/239; 544/241
[58] Field of Search .......................... 514/85; 544/232; 546/22

[56] References Cited

U.S. PATENT DOCUMENTS

| | | | |
|---|---|---|---|
| 3,225,044 | 12/1965 | Dauterman et al. | 544/232 |
| 3,309,371 | 3/1967 | Currey et al. | 544/232 |
| 3,878,210 | 4/1975 | Lorenz | 544/232 |
| 4,140,768 | 2/1979 | Fuchs et al. | 544/232 |
| 4,303,652 | 12/1981 | Jones et al. | 544/232 |

FOREIGN PATENT DOCUMENTS 2700019 7/1977 Fed. Rep. of Germany .
140092 8/1983 Japan .

OTHER PUBLICATIONS

Derwent Abstract for Japan Patent No. 140092 (8/19/83).
Takeshiba et al., *Agr. Biol. Chem.*, 38, p. 1177 (1974).

*Primary Examiner*—Donald G. Daus
*Assistant Examiner*—E. Bernhardt
*Attorney, Agent, or Firm*—Wenderoth, Lind & Ponack

[57] ABSTRACT

Organic phosphates of the formula:

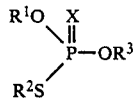

wherein $R^1$ and $R^2$ are respectively an alkyl group; $R^3$ is a phenyl group which is substituted at least by a pyridazinyloxy or pyridazinylthio group in which the pyridazinyl group may be substituted; and X is an oxygen or sulfur atom, or a salt thereof, have marked insecticidal-acaricidal activity against plant pests and mites, household pests, with very low toxicity to warm-blooded animals and fish.

12 Claims, No Drawings

PYRIDAZINYLOXY (OR THIO) PHENYL PHOSPHATES

The present invention relates to organic phosphates. More particularly, the present invention relates to a compound of the formula:

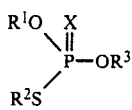
(I)

wherein $R^1$ and $R^2$ are respectively an alkyl group; $R^3$ is a phenyl group which is substituted at least by a pyridazinyloxy or pyridazinylthio group in which the pyridazinyl group may be substituted; and X is an oxygen or sulfur atom, or a salt thereof (this compound may be hereinafter referred to as the compound (I) of the present invention).

The present inventors had found that organic phosphates of the formula:

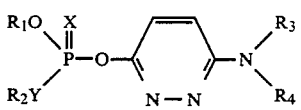

wherein $R_1$ and $R_2$ are same or different lower alkyl; $R_3$ and $R_4$ are same or different H, lower alkyl, lower alkenyl, lower alkanoyl or lower alkoxy-lower alkyl, or $R_3$ and $R_4$, taken together, form a 5- or 6-membered heterocyclic ring; X is O or S, Y is O, S, imino or a single bond show insecticidal and acaricidal effect against agriculturally harmful insects and hygienically harmful insects and mites (e.g. Japanese published unexamined patent application No. 140,092/1983).

However, the insecticidal-acaricidal effect of the phosphates is not yet satisfactory for applying practically.

The present inventors have conducted intensive research to obtain a compound which is safer for mammals and which has a stronger insecticidal-acaricial activity, and as a result, unexpectedly found that the compound of the structural formula having a group of the formula

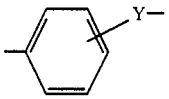

wherein Y is oxygen or sulfur between the moieties

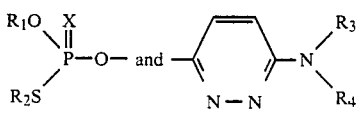

in the known compound described in Japanese published unexamined patent application No. 140,092/1983, i.e. the compound (I) of the present invention shows more excellent insecticidal-acaricidal activity than the above known phosphates. Based on these findings, the intensive research has been further continued and as a result culminated in the present invention.

Thus, the compound (I) of the present invention has superior insecticidal-acaricidal activity to the known compounds. Furthermore, the drug damage to plant as well as toxicity to warm-blooded animal and fish of the compound (I) of the present invention is less than those of the known compounds. The compound (I) of the present invention has marked insecticidal-acaricidal activity against especially pests damaging vegetables, such as cabbage or Chinese cabbage.

This activity manifests not only when the compound (I) of the present invention is directly applied to insects and mites, for example by spraying it on host plants, but also when the compound (I) of the present invention absorbed by plants from the roots, leaves, stems or the like comes into contact with the pests as, for example, the pests suck on or gnaw the plant.

Referring to the formula (I), the alkyl group $R^1$ or $R^2$ is a straight-chain or branched lower alkyl group of 1 to 6 carbon atoms, such as methyl, ethyl, n-propyl, isopropyl, n-butyl, isobutyl, sec-butyl, tert-butyl, n-pentyl, sec-pentyl, isopentyl, neopentyl, n-hexyl, or isohexyl.

Referring to the substituent $R^3$, the phenyl group which is substituted at least by a pyridazinyloxy or pyridazinylthio group in which the pyridazinyl group is substituted is a phenyl group which is substituted at least by a pyridazinyloxy or pyridazinylthio group which is substituted on the pyridazine ring by one or more substituents, such as a halogen atom, an alkyl group, an alkoxy group, an alkylthio group or a group of the formula

wherein $R^6$ and $R^7$ are respectively a hydrogen atom, an alkyl group or an acyl group. Desirably $R^3$ is a phenyl group which is substituted at least by a pyridazinyloxy or pyridazinylthio group which is substituted on the pyridazine ring by one to two substituents as defined above.

Referring to the substituent on the pyridazine ring, the alkyl group is a straight-chain or brancehd lower alkyl group of 1 to 6 carbon atoms, e.g. methyl, ethyl, n-propyl, isopropyl, n-butyl, isobutyl, sec-butyl, tert-butyl, n-pentyl, sec-pentyl, isopentyl, neopentyl, n-hexyl or isohexyl; the alkoxy group is a straight-chain or branched lower alkoxy group of 1 to 6 carbon atoms, e.g. methoxy, ethoxy, n-propoxy, isopropoxy, n-butoxy, isobutoxy, sec-butoxy, tert-butoxy, n-pentyloxy, sec-pentyloxy, isopentyloxy, neopentyloxy, n-hexyloxy or isohexyloxy; the alkylthio group is a straight-chain or branched lower alkylthio group of 1 to 6 carbon atoms, e.g. methylthio, ethylthio, n-propylthio, isopropylthio, n-butylthio, isobutylthio, sec-butylthio, tert-butylthio, n-pentylthio, sec-pentylthio, isopentylthio, neopentylthio, n-hexylthio, or isohexylthio; the halogen atom is fluorine, chlorine, bromine or iodine; and the acyl group is an acyl group derived from a straight-chain or branched, cyclic organic carboxylic acid which may contain an unsaturated bond, a nitrogen atom, an oxygen atom, a sulfur atom, etc., preferably is an aliphatic acyl group of 1 to 6 carbon atoms, e.g. formyl, acetyl, propionyl, 2,2-dimethylpropionyl, butyryl, 3-methylbutyryl, pentanoyl or hexanoyl.

In the above formula, $R^1$ is preferably an alkyl group of 1 to 3 carbon atom, such as methyl, ethyl, n-propyl or isopropyl, more preferably is methyl or ethyl. $R^2$ is preferably an alkyl group of 1 to 4 carbon atoms, such as methyl, ethyl, n-propyl, isopropyl, n-butyl, isobutyl or sec-butyl, more preferably is n-propyl, isopropyl, n-butyl, isobutyl or sec-butyl. $R^3$ is preferably a group of the formula:

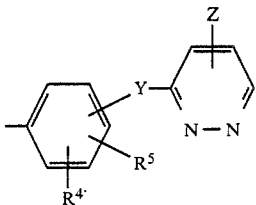

wherein $R^4$ and $R^5$ are respectively a hydrogen atom or an alkyl group; Z is a hydrogen atom, a halogen atom, an alkyl group, an alkoxy group, an alkylthio group, or a group of the formula

in which $R^6$ and $R^7$ are respectively a hydrogen atom, an alkyl group or an acyl group; and Y is an oxygen or sulfur atom.

More preferably, $R^3$ is a group of the formula:

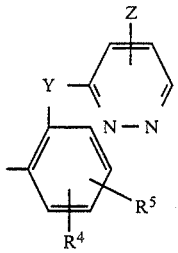

wherein the symbols have the same meanings as defined above.

Referring to the definitions of $R^4$, $R^5$, Y and Z, preferably $R^4$ is a hydrogen atom; $R^5$ is a hydrogen atom or an alkyl group; Y is an oxygen atom; and Z is a hydrogen atom, a halogen atom, an alkyl group or an alkoxy group.

Furthermore, in a group of the formula:

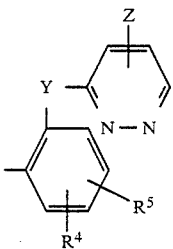

preferably, $R^4$ and $R^5$ are respectively a hydrogen atom; Y and Z have the same meaning as defined above.

In the above formulas the substituents $R^4$, $R^5$, and Y may be located at arbitrary positions on the phenyl ring, and the substituent Z may be located at an arbitrary position on the pyridazinyl ring, preferably at the 3-position on the pyridazinyl ring. The alkyl group, halogen atom, alkoxy group, alkylthio group, acyl group for $R^4$, $R^5$, or Z have the same meanings as defined above with reference to the substituent on the pyridazine ring.

The compound (I), when it contains an amino group in the substituent represented by $R^3$, may form an addition salt with an inorganic acid, such as hydrochloric acid, sulfuric acid or phosphoric acid, or with an organic acid, such as acetic acid, benzenesulfonic acid, p-toluenesulfonic acid, methanesulfonic acid, citric acid, tartaric acid, oxalic acid, propionic acid, maleic acid, malic acid, malonic acid, fumaric acid, mandelic acid or ascorbic acid.

The compound (I) of the present invention is effective in the control of plant-damaging insects, mites parasitic on plants and animals, and household pests.

A compound of the formula (I) or a salt thereof has marked insecticidal-acaricidal effect on a wide variety of plant-damaging insects, parasitic mites on plants and animals, household pests, etc. with a low oral toxicity to warm-blooded animals and fish, and that it can be produced advantageously on an industrial scale.

A compound of the present invention can be safely applied without presenting any substantial drug damage to plants (i.e. without substantial phytotoxicity) and, without substantial toxicity to fish or warm-blooded animals.

The compound (I) of the present invention as well as any suitable composition containing it is particularly effective in the control of pests including, but not limited thereto, insects of the order Hemiptera, such as *Eurydema rugosa, Scotinophara lurida, Riptortus clavatus, Stephanitis nashi, Laodelphax stiatellus, Nephotettix cincticeps, Unaspis yanonensis, Aphis glycines, Lipaphis pseudobrassicase, Brevicoryne brassicae* or *Aphis gossypii;* insects of the order Lepidoptera, such as *Spodoptera litura, Plutella xylostella, Pieris rape crucivora, Chilo suppressalis, Plusia nigrisigna, Eelicoverpa assulta, Leucania separata, Mamestra brassicae, Adoxophyes orana, Syllepte derogata, Cnaphalocrocis medinalis,* or *Phthorimaea operculella;* insects of the order Coleoptera, such as *Epilachna vigintioctopunctata, Aulacophora femoralis, Phyllotreta striolata, Oulema orgzae* or *Echinocnemus squameus;* insects of the order Diptera, such as *Musca domestica, Culex pipiens pallens, Tabanus trigonus, Hylemya antiqua* or *Hylemya platura;* insects of the order Orthoptera, such as *Locusta migratoria* or *Gryllotalpa arricana;* insects of the order Blattidae, such as *Blatella germanica* or *Periplaneta fuliginosa;* mites of the order Tetranychidae, such as *Tetranychus urticae, Panonychus citri, Tetranychus kanzawai, Tetranychus cinnabarinus, Panonychus ulmi,* or *Aculus Pelekassi;* and nematodes, such as *Aphelenchoides besseyi.*

The compound (I) of the present invention displays a marked controlling activity particularly against insects of the order Lepidoptera and mites.

For use as an insecticidal-acaricidal agent, the compound (I) of the present invention may employ any of the known application formulations for agricultural chemicals. Thus, for example, one or more species of compound (I) of the present invention are dissolved or dispersed in a suitable liquid carrier or admixed with, or adsorbed on, a suitable solid carrier to prepare an emulsifiable concentrate, oil solution, spray, wettable powder, dust, granule, tablet, ointment or the like. If necessary, emulsifiers, suspension aids, spreading agents, penetrating agents, wetting agents, thickeners, stabilizers, etc. may also be incorporated in such compositions. These preparations can be produced by per se known manufacturing methods.

The concentration of active compound (I) of the present invention in the insecticidal-acaricidal composition may vary with intended uses. Thus, while the concentration may desirably be in the range of about 10 to 90 weight % in the case of emulsifiable concentrates, wettable powders, etc., about 0.1 to 10 weight % in the case of oil solutions, dusts, etc. and about 1 to 20 weight % in the case of granules, these concentrations may be modified according to the intended application. As for emulsifiable concentrates, wettable powders, etc., they are applied after diluting (e.g. 100 to 100000-fold) at site using a diluent such as water.

Examples of said liquid carrier (solvent) include water; alcohols, e.g. methyl alcohol, ethyl alcohol, n-propyl alcohol, isopropyl alcohol or ethylene glycol; ketones, e.g. acetone or methylethyl ketone; ethers, e.g. dioxane, tetrahydrofuran, ethylene glycol monomethyl ether, diethylene glycol monomethyl ether or propylene glycol monomethyl ether; aliphatic hydrocarbons, e.g. kerosin, kerosene, fuel oil or machine oil; aromatic hydrocarbons, e.g. benzene, toluene, xylene, solvent naphtha or methyl naphthalene; halogenated hydrocarbons, e.g. methylene chloride, chloroform or carbon tetrachloride; acid amides, e.g. dimethylformamide or dimethylacetamide; esters, e.g. ethyl acetate, butyl acetate, or glycerol ester of fatty acid; and nitriles, e.g. acetonitrile and propronitrile. These solvents may be used alone or as a mixture of two or more species in an appropriate ratio.

Examples of said solid carrier (diluents) include vegetables powders, such as soybean powder, tobacco powder, wheat flour or sawdust; mineral powders, such as clays (e.g. kaolin, bentonite or acid clay) talcs (e.g. steatite powder or agalmatolite) or siliceous materials (e.g. diatomaceous earth or mica powder); alumina; sulfur power; or activated carbon. These solid carriers may be used alone, or as a mixture of two or more species in an appropriate ratio.

Examples of the ointment base include polyethylene glycol; pectin; polyhydric alcohol esters of higher fatty acid, such as glycerol ester of monostearic acid; cellulose derivatives, such as methyl cellulose; sodium alginate; bentonite; higher alcohols; polyhydric alcohols, such as glycerol; vaseline; white petrolatum; liquid paraffin; lard; vegatable oils; hydrous lanolin; anhydrous lanolin, hardened oils; and resins. These bases may be used alone or as a mixture of two or more species. These may be used with the following surfactants.

The surfactants which may be used as said emulsifiers, speading agents, penetrating agents, dispersing agents, etc. include nonionic or anionic surfactants, such as soaps; polyoxyethylene alkylaryl ethers (e.g. Noigen EA 142 ® from Dai-ichi Kogyo Seiyaku K.K., Japan); polyoxyethylene aryl esters (e.g. Nornal ® from Toho Chemical K.K., Japan); alkylsulfates (e.g. Emal 10 ® and Emal 40 ® from Kao Soap K.K., Japan); alkyl sulfonates (e.g. Neogen ® and Neogen T ® from Dai-ichi Kogyo Seiyaku Co. and Neopelex ® from Kao Soap K.K.); polyethylene glycol ethers (e.g. Nonipol 85 ®, Nonipol 100 ®, Nonipol 160 ® from Sanyo Kasei K.K., Japan); or polyhydric alcohol esters (e.g. Tween 20 ® and Tween 80 ® from Kao Soap K.K.).

The compound (I) of the present invention may also be used in admixture with other insectides (e.g. pyrethroid, organophosphorus, carbamate, natural and other insectides), acaricides, nematocides, herbicides, plant hormones, plant growth regulators, synergists, attractants, fungicide, repellants, colorants, fertilizers, etc.

The emulsifiable concentrate and wettable powder containing the compound (I) of the present invention may be preferably diluted to a concentration of about 50 to 1,000 ppm before their application.

When the compound (I) of the present invention is used as an agricultural insecticide, the insecticide may be preferably applied so that about 30 to 500 g of the compound (I) of the present invention are spread per 10 are. The composition containing the compound (I) of the present invention may be applied to plants according to per se known methods, e.g. it may be spread directly over stems and leaves, or applied near the root.

The insecticide may be sprayed by using an appropriate sprayer, and also be used in the form of an insecticidal aerosol by adding jet agents, such as freon, liquefied petrolic gas, dimethyl ether or carbon dioxide gas.

The composition containing the compound (I) of the present invention is effective against pests damaging vegetables (e.g. cabbage, Chinese cabbage, cucumbers, potatoes), fruit trees (e.g. citrus, pears), flowers (e.g. roses, chrysanthemums), and tobacco; for example the cabbage armyworm, the common cabbage worm, the diamondback moth, aphids, the 28-spotted ladybettle (larva), the potato tuberworm, the smaller tea tortrix, the arrow-head scale, the horned wax scale, the tortrix, and the tobacco budworm, when it is applied at the time of the appearance of these pests.

The compound (I) of the present invention may be produced by per se known methods. For example it can be produced by reacting a compound of the formula:

$$HOR^3 \qquad (II)$$

wherein $R^3$ has the same meaning as defined above, or a salt thereof, with a compound of the formula:

$$\begin{array}{c} R^1O \\ \phantom{R^2S}\diagdown \!\!\!\!\!\overset{X}{\underset{}{\|}} \\ \phantom{R^2S}\phantom{\diagdown}P\!-\!Hal \\ R^2S\diagup \end{array} \qquad (III)$$

wherein Hal is a halogen atom; and the other symbols have the same meanings as defined above.

The halogen atom represented by Hal is fluorine chlorine or bromine.

The compound (II) may be used as a salt with an alkali metal, such as sodium or potassium, since it has a hydroxyl group in the molecule.

The salt of the compound (II) may be represented by the formula:

$$M'OR^3$$

wherein $R^3$ has the same meaning as defined above and M' is an alkali metal. Examples of the alkali metal include sodium and potasium. When the amino group is contained in the substituents $R^3$ in the compound (II) or a salt thereof, the amino group may form an addition salt with an inorganic acid, such as hydrochloric acid, sulfuric acid or phosphoric acid.

In this reaction, the compound (III) may be used in an amount of about 0.5 to 3 moles preferably about 1 to 1.5 moles, per mole of the compound (II) or a salt thereof.

This reaction is usually conducted in a solvent inert to the reaction. Examples of the solvent include among others, water; alcohols, e.g. methanol, ethanol, n-propanol, isopropanol, n-butanol or t-butanol; aromatic hydrocarbons, e.g. benzene, toluene or xylene; halogenated hydrocarbons, e.g. methylene chloride, chloroform or carbon tetrachloride; ethers, e.g. ethyl ether, dioxane or tetrahydrofuran; ketones, e.g. acetone or methylethyl ketone; nitriles, e.g. acetonitrile or propionitrile; amides, e.g. dimethylformamide, dimethylacetamide or hexamethylphosphoramide; esters, e.g. methyl acetate, ethyl acetate, or butyl acetate; and sulfoxides, e.g. dimethylsulfoxide. These solvents may be used alone or as a mixture of two or more species. When these solvents are used as a mixture of two or more species, not only the combination of those solvents which can be mixed uniformly with each other, but also the combination of those solvents which can not be mixed uniformly with each other, such as the combination of water and the said aromatic hydrocarbons, or the combination of water and the said halogenated hydrocarbons may be used.

This reaction is conducted preferably in the presence of an acid-binding agent so that the reaction proceeds smoothly.

Employed as the acid-binding agent is an organic base, such as tri-(alkyl group of 1 to 6 carbon atoms)-substituted amines, e.g. trimethylamine or triethylamine; tertiary amines, e.g. pyridine or γ-collidine; alkali metal alcoholates, e.g. sodium methylate, sodium ethylate or potassium ethylate; or, an inorganic base, such as alkali metal hydroxides, e.g. potassium hydroxide or sodium hydroxide; alkaline earth metal hydroxides, e.g. calcium hydroxide; alkali metal carbonates, e.g. potassium carbonate or sodium carbonate; alkali metal bicarbonates, e.g. potassium bicarbonate or sodium bicarbonate; or alkaline earth metal carbonates, e.g. calcium carbonate.

In this reaction, the acid-binding agent may be used in an amount of about 0.7 to 2 moles per mole of the compound (II) or a salt thereof.

The reaction temperature may be chosen in a range of about −20° C. to 150° C., but is usually about 0° C. to 100° C. The reaction goes to completion in about 30 minutes to 10 hours. The end-point of reaction can be ascertained by thin layer chromatography or high performance liquid chromatography.

This reaction may be carried out either by first adding the compound (II) or a salt thereof to the solvent, and then adding the compound (III) to the mixture, where a base may be added if necessary, or by first adding and dissolving the compound (II) in a base solution, and then adding the compound (III) to the solution, where a base may be added if necessary.

The compound (I) or a salt thereof can also be produced by reacting a compound of the formula:

$$HOR^1 \quad (IV)$$

wherein $R^1$ has the same meaning as defined above, or an alcoholate thereof, with a compound of the formula:

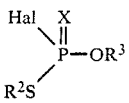

(V)

wherein Hal is a halogen atom; and other symbols have the same meanings as defined above. The halogen atom represented by Hal is fluorine, chlorine or bromine.

As the alcoholate of the compound (IV), use is made of a compound of the formula:

$$M'OR^1$$

wherein $R^1$ has the same meaning as defined above; and M' is an alkali metal. Examples of the alkali metal include sodium and potassium.

When an amino group is contained in the substituent represented by $R^3$ in the compound (V), the amino group may form an acid-addition salt with an inorganic acid, such as hydrochloric acid, sulfuric acid or phosphoric acid.

The compound (V) or a salt thereof is used in an amount of about 0.5 to 3 moles per mole of the compound (IV) or an alcoholate thereof. This reaction may be conducted in the same manner as the reaction of the compound (II) or a salt thereof with the compound (III) as mentioned above.

This reaction is usually conducted in a solvent inert to the reaction. Examples of the solvent include among others, water; alcohols, e.g. methanol, ethanol, n-propanol, isopropanol, n-butanol or t-butanol; aromatic hydrocarbons, e.g. benzene, toluene or xylene; halogenated hydrocarbons, e.g. methylene chloride, chloroform or carbon tetrachloride; ethers, e.g. ethyl ether, dioxane or tetrahydrofuran; ketones, e.g. acetone or methylethyl ketone; nitriles, e.g. acetonitrile or propionitrile; amides, e.g. dimethylformamide, dimethylacetamide or hexamethylphosphoramide; esters, e.g. methyl acetate, ethyl acetate, or butyl acetate; and sulfoxides, e.g. dimethylsulfoxide. These solvents may be used alone or as a mixture of two or more species. When these solvents are used as a mixture of two or more species, not only the combination of those solvents which can be mixed uniformly with each other, but also the combination of those solvents which can not be mixed uniformly with each other, such as the combination of water and the aromatic hydrocarbons, or the combination of water and the halogenated hydrocarbons may be used.

This reaction is conducted preferably in the presence of an acid-binding agent so that the reaction proceeds smoothly.

Examples of the acid-binding agent is an organic base, such as tri-(alkyl group of 1 to 6 carbon atoms)-substituted amines, e.g. trimethylamine or triethylamine; tertiary amines, e.g. pyridine or γ-collidine; alkali metal alcoholates, e.g. sodium methylate, sodium ethylate or potassium ethylate; or, an inorganic base, such as alkali metal hydroxides, e.g. potassium hydroxide or sodium hydroxide; alkaline earth metal hydroxides, e.g. calcium hydroxide; alkali metal carbonates, e.g. potassium carbonate or sodium carbonate; alkali metal bicarbonates, e.g. potassium bicarbonate or sodium bicarbonate; or alkaline earth metal carbonates, e.g. calcium carbonate.

In this reaction, the acid-binding agent may be used in an amount of about 0.7 to 2 moles per mole of the compound (IV) or an alcoholate thereof.

The reaction temperature may be chosen in a range of about −20° C. to 150° C., but is usually about 0° C. to 100° C. The reaction goes to completion in about 30 minutes to 10 hours. The end-point of reaction can be ascertained by thin layer chromatography, high performance liquid chromatography, etc.

A compound of the formula:

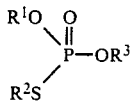  (I')

wherein the symbols have the same meanings as defined above, or a salt thereof, that is the compound (I) of the present invention wherein X is an oxygen atom can be produced by reacting a thiophosphate of the formula:

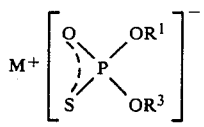  (VI)

wherein M is an alkali metal, an alkaline earth metal or an ammonium radical; and the other symbols have the same meanings as defined above with a compound of the formula:

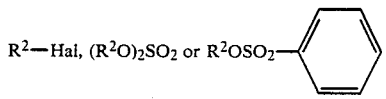  (VII)

[wherein the symbols have the same meanings as defined above]; and Hal is a halogen atom.

Referring to the above formulas, the halogen atom Hal is fluorine, chlorine, bromine or iodine. The alkali metal represented by M is lithium, sodium or potassium, and the alkaline earth metal represented by M is magnesium or calcium, and the ammonium radical represented by M is an unsubstituted ammonium radical or mono- to tri-(alkyl group of 1 to 6 carbon atoms)-substituted ammonium radical, such as trimethylammonium, triethylammonium, tripropylammonium, dimethylammonium, diethylammonium, dipropylammonium or monomethylammonium. The dotted portion in the formula (VI) shows that electrons are delocalized. The compound (VI) may also be shown by the following structural formula:

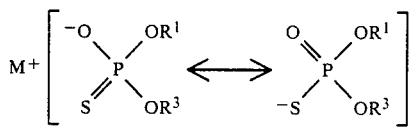

When an amino group is contained in the substituent represented by $R^3$ in the compound (VI), the amino group may form an acid addition salt with an inorganic acid, such as hydrochloric acid, sulfuric acid or phosphoric acid.

In this reaction, examples of the compound (VII) is methyl iodide, ethyl iodide, n-butyl bromide, dimethyl sulfate, diethyl sulfate, di-n-butyl sulfate, methyl benzenesulfonate, ethyl benzenesulfonate, n-propyl beanzenesulfonate or n-butyl benzenesulfonate.

The compound (VII) is used in an amount of about 0.5 to 3 moles per mole of the compound (VI).

This reaction is conducted in a solvent inert to the reaction. Examples of the solvent include among others, water; alcohols, e.g. methanol, ethanol, n-propanol, isopropanol, n-butanol or t-butanol; aromatic hydrocarbons, e.g. benzene, toluene or xylene; halogenated hydrocarbons, e.g. methylene chloride, chloroform or carbon tetrachloride; ethers, e.g. ethyl ether, dioxane or tetrahydrofuran; ketones, e.g. acetone or methylethyl ketone; nitriles, e.g. acetonitrile or propionitrile; amides, e.g. dimethylformamide, dimethylacetamide or hexamethylphosphoramide; esters, e.g. methyl acetate, ethyl acetate, or butyl acetate; and sulfoxides, e.g. dimethylsulfoxide.

Reaction temperature can be chosen in the range of about −20° C. to 150° C.; but the reaction temperature is generally about 0° C. to 100° C. The reaction goes to completion in a period of from about 30 minutes to 10 hours. When the substituents $R^2$ in the compound (VII) is a branched lower alkyl group, e.g. isopropyl, a longer reaction time is required, i.e. about 1 to 20 hours. The end-point of reaction can be ascertained by thin layer chromatography, high performance liquid chromatography.

When the compound (I) is obtained in the form of a free form, it may be converted to a salt of the compound (I) by per se known methods, and when the compound (I) is obtained in the form of a salt, it may be converted to a free form of the compound (I) by per se known methods, and then if necessary the free form may be converted to a salt of the compound (I) by per se known methods.

The compounds (I), (I'), or their salts may be separated and purified by per se known methods, such as concentration, concentration under reduced pressure, distillation under reduced pressure, pH adjustment, solvent transformation, solvent extraction, crystallization, recrystallization or chromatography.

Phosphate halide represented by the formula (III) or (V), or a salt thereof, which is used for starting materials, can easily be produced by per se known methods or the similar methods.

For example, the compound (III), the compound (V) or a salt thereof, can be produced from the known compound (VIII) according to the following scheme.

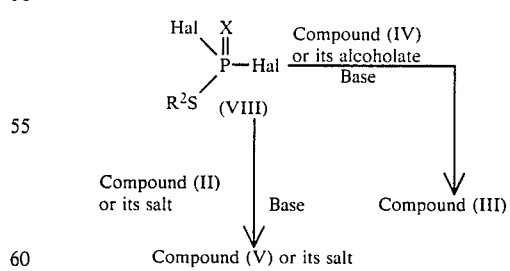

In the above formulas the symbols have the same meanings as defined above.

That is, the compound (III) can be produced by reacting the compound (VIII) with the compound (IV) or an alcholate thereof, and the compound (V) or a salt thereof can be produced by reacting the compound (VIII) with the compound (II) or a salt thereof.

In these reactions, the compound (VIII) is used in an amount of about 1 to 1.5 moles per mole of compound (II) or a salt thereof, or the compound (IV) or an alcholate thereof. These reaction can be carried out by the same manner.

These reactions are conducted in a solvent inert to the reactions. Examples of the solvent include among others water; alcohols, e.g. methanol, ethanol, n-propanol, isopropanol, n-butanol or t-butanol; aromatic hydrocarbons, e.g. benzene, toluene or xylene; halogenated hydrocarbons, e.g. methylene chloride, chloroform or carbon tetrachloride; ethers, e.g. ethyl ether, dioxane or tetrahydrofuran; ketones, e.g. acetone or methylethyl ketone; nitriles, e.g. acetonitrile or propionitrile; amides, e.g. dimethylformamide, dimethylacetamide or hexamethylphosphoramide; esters, e.g. methyl acetate, ethyl acetate, or butyl acetate; and sulfoxides, e.g. dimethylsulfoxide.

These reactions are carried out preferably in the presence of an acid-binding agent i.e. a base. Examples of the acid-binding agent include an organic base, such as tri-(alkyl group of 1 to 6 carbon atoms)-substituted amines, e.g. trimethylamine or triethylamine; tertiary amines, e.g. pyridine or γ-collidine; alkali metal alcoholates, e.g. sodium methylate, sodium ethylate, or potassium ethylate; and an inorganic base, such as alkali metal hydroxides, e.g. potassium hydroxide or sodium hydroxide; alkaline earth metal hydroxides, e.g. calcium hydroxide; alkali metal carbonates, e.g. potassium carbonate or sodium carbonate; alkali metal bicarbonates, e.g. potassium bicarbonate or sodium bicarbonate; or alkaline earth metal carbonates, e.g. calcium carbonate.

In these reactions, the acid-binding agent is preferably used in an amount of about 0.7 to 2 moles per mole of the compound (II) or compound (IV).

Reaction temperature can be chosen in a range of about −20° C. to 150° C., but the reaction temperature is preferably about 0° C. to 100° C. The reactions goes to completion in a period of from 30 minutes to 10 hours.

The compound (VI) as the starting material, can be produced by per se known methods. For example, it can be produced according to the known methods described in U.S. Pat. No. 4,474,775 or the following method.

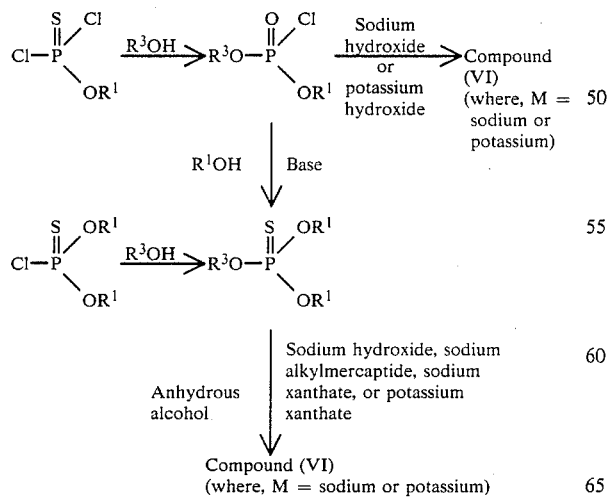

The compound (II) or a salt thereof, as a starting material, can be produced by per se known methods or the similar methods, e.g. the method described in Japanese published unexamined patent application No. 122234/1979, and U.S. Pat. No. 4,264,769.

In addition the present inventors carried out the research work on novel processes of producing the compound of the formula (II) wherein $R^3$ is a group of the formula:

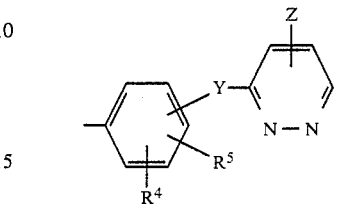

wherein $R^4$ and $R^5$ are respectively a hydrogen atom or an alkyl group; Z is a hydrogen atom, a halogen atom, an alkyl group, an alkoxy group, an alkylthio group or a group of the formula

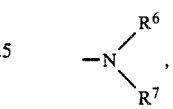

where $R^6$ and $R^7$ are respectively a hydrogen atom, an alkyl group or an acyl group; Y is an oxygen or sulfur atom (this compound is hereinafter referred to as the compound (II′)), which is industrially advantageous, and found out the route described below in which the compound of the formula (II′) or its salt can be obtained in a high yield and under mild condition.

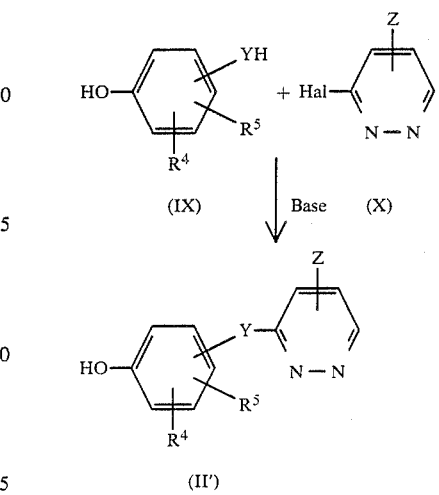

wherein Hal is a halogen atom, such as chlorine or bromine; and other symbols have the same meanings as defined above.

Examples of the salt of the compound (II′) include a salt with an alkali metal, such as sodium or potassium.

In the formulas (IX), (X) and (II′), preferably $R^4$ and $R^5$ are respectively a hydrogen atom; Y is an oxygen atom, and Z is of same meaning as defined above, with a proviso that hydrogen or chlorine is excluded. More preferably Z is a bromine atom, an alkyl group, an alkoxy group, an alkylthio group, or a group of the formula

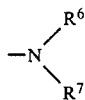

wherein $R^6$ and $R^7$ are respectively a hydrogen atom, an alkyl group, or an acyl group; and Y is an oxygen or sulfur atom.

In the difinitions of these formulas, the alkyl group, the alkoxy group, the alkylthio groups, and the acyl group have the same meaning as defined above mentioned with reference to the substituted on the pyridazine ring.

Having a hydroxy group or a thiol group within its molecule, the compound (IX) may be used as a salt with an alkali metal, such as sodium or potassium. When an amino group is contained in the substituent represented by Z in the compound (X), the amino group may form of an addition salt with an inorganic acid, such as hydrochloric acid, sulfuric acid or phosphoric acid.

The compound (X) or a salt thereof is used in an amount of about 0.5 to 3 moles per mole of the compound (IX) or a salt thereof.

This reaction is usually carried out in a solvent inert to the reaction. Examples of the solvent include a neutral polar solvent, such as nitriles, e.g. acetonitrile or propionitrile; amides, e.g. dimethylformamide, dimethylacetamide, or hexamethylphosphoramide; nitromethane; dimethylsulfoxide; tetramethylene sulfone; and N-methyl pyrrolidone. These solvents may be used alone, or as a mixture of two or more species.

It is preferable that this reaction is conducted in the presence of a base. Examples of the base include an inorganic base, such as alkali metal hydroxides, e.g. potassium hydroxide or sodium hydroxide; alkaline earth metal hydroxides, e.g. calcium hydroxide; alkali metal carbonates, e.g. potassium carbonate or sodium carbonate; alkali metal bicarbonates, e.g. potassium bicarbonate or sodium bicarbonate; and alkaline earth metal carbonates, e.g. calcium carbonate.

The base may be used in an amount of about 0.7 to 1 moles per mole of the compound (IX) or a salt thereof.

Reaction temperature ranges from about 20° C. to 200° C., preferably from about 50° C. to 140° C. The reaction goes to completion in a period of from about 30 minutes to 6 hours. The compound (II') wherein Z is a hydrogen atom, can be produced by hydrogenating the compound (II') wherein Z is a halogen atom in the presence of a catalyst, such as Pd-C.

This hydrogenation reaction is carried out by per se known methods, or the similar methods.

The compound (II') or its salt may be separated and purified by per se known methods, such as concentration, concentration under reduced pressure, distillation under reduced pressure, pH adjustment, solvent transformation, solvent extraction, crystallization, recrystallization or chromatography.

The compound (II') or its salt is useful as a starting material for the compound (I) of the present invention, which exerts an insecticidal-acaricidal activity.

The following examples are intended to illustrate the present invention in further detail and should by no means be construed to delimit the scope of the invention.

EXAMPLE 1

O-Methyl-S-sec-butyl-O-[2-(3-chloropyridazinyl-6-oxy)phenyl]phosphorothioate (Compound No. 27)

11.1 g of 3-chloro-6-(2-hydroxyphenoxy)pyridazine and 6.1 g of triethylamine are dissolved in 70 ml of acetone, followed by addition of 11.1 g of O-methyl-S-sec-butylphosphorochloridothioate dropwise at 5° to 10° C. The mixture is stirred at room temperature for 4 hours. The resulting crystals of triethylamine hydrochloride are filtered off and the filtrate is then concentrated under reduced pressure.

The resulting residue is dissolved in toluene and the toluene solution is washed with water. The toluene is evaporated off under reduced pressure, and the resulting reddish barown oily substance is purified by column chromatography (silica gel: Wakogel C-300® produced by Wako Pure Chemical Co.; eluent: n-hexane/acetone=¼v/v) to yield 12.7 g of a light-yellow oily title compound.

Yield: 66%.
$n_D^{25} = 1.5539$.

EXAMPLE 2

O-Ethyl-S-n-propyl-O-[2-(3-chloropyridazinyl-6-thio)-phenyl]phosphorodithioate (Compound No. 32)

3.4 g of potassium hydroxide are dissolved in 70 ml of isopropanol, followed by addition of 11.9 g of 3-chloro-6-(2-hydroxyphenylthio)pyridazine. To the mixture, 12.0 g of O-ethyl-S-n-propylphosphorochloridodithioate are added dropwise with stirring. After stirring at 40° to 45° C. for 3 hours, the isopropanol is evaporated off under reduced pressure. The residue is dissolved in toluene, and then washed with water, 1N NaOH, and water in that order. The toluene is evaporated off under reduced pressure. The resulting yellow oily substance is purified by column chromatography in the same manner as shown in Example 1 to yield 16.6 g of a light-yellow oily title compound.

Yield: 79%.
$n_D^{25} = 1.6139$.

EXAMPLE 3

O-Ethyl-S-n-propyl-O-[3-(3-dimethylaminopyridazinyl-6-oxy)phenyl]phosphorothioate (Compound No. 21)

11.6 g of 3-dimethylamino-6-(3-hydroxyphenoxy)pyridazine and 6.1 g of triethylamine are dissolved in 80 ml of acetone, followed by addition of 11.1 g of O-ethyl-S-n-propylphosphorochloridothioate dropwise with stirring. The mixture is stirred at 40° to 45° C. for 3 hours, and then subjected to the same process as shown in Example 1 to yield 10.5 g of a yellow oily title compound.

Yield: 53%.
$n_D^{25} = 1.5641$.

EXAMPLE 4

O-Ethyl-S-n-propyl-O-[4-(3-chloropyridazinyl-6-oxy)-phenyl]phosphorothioate (Compound No. 2)

11.1 g of O-ethyl-S-n-propylphosphorochloridothioate are added to a solution of the mixture consisting of 11.1 g of 3-choloro-6-(4-hydroxyphenoxy)pyridazine and 6.1 g of triethylamine in 70 ml of acetone. The mixture is stirred at 40° to 45° C. for 3 hours.

The resulting mixture, after being subjected to the same process as shown in Example 1, is purified by column chromatography to yield a light-yellow oily substance. This substance, when kept untreated, crystallizes to yield 11.3 g of a white crystalline title compound.

Yield: 58%.
m.p.=51°–53° C.

EXAMPLE 5

O-Ethyl-S-n-propyl-O-[2-(3-chloropyridazinyl-6-oxy)-phenyl]phosphorodithioate (Compound No. 30)

3.4 g of potassium hydroxide are dissolved in 80 ml of isopropanol, followed by addition of 11.1 g of 3-chloro-6-(2-hydroxyphenoxy)pyridazine. While stirring, 12.0 g of O-ethyl-S-n-propylphosphorochloridothioate are added into the mixture. The resulting mixture is stirred at 35° to 40° C. for 3 hours, and then treated in the same manner as shown in Example 2 to yield 17.0 g of a white crystalline title compound.

Yield: 84%.
m.p.=66°–67.5° C.

The compounds which is produced by the same manner as shown in Examples 1 to 5, inclusive of the compounds produced in Examples 1 to 5, are listed in Tables 1 to 4.

TABLE 1

Formula

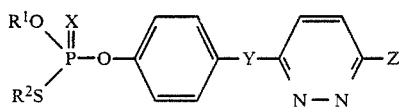

| Compound No. | $R^1$ | $R^2$ | X | Y | Z | Appearance | $n_D^{25}$ or (m.p.) |
|---|---|---|---|---|---|---|---|
| 1 | $C_2H_5$ | n-$C_3H_7$ | O | O | H | colorless oil | 1.5552 |
| 2 | $C_2H_5$ | n-$C_3H_7$ | O | O | Cl | colorless crystal | (51–53° C.) |
| 3 | $C_2H_5$ | n-$C_3H_7$ | S | O | Cl | pale yellow oil | 1.5875 |
| 4 | $C_2H_5$ | n-$C_3H_7$ | O | S | Cl | pale yellow oil | 1.5861 |
| 5 | $C_2H_5$ | n-$C_3H_7$ | S | S | Cl | pale yellow oil | 1.6112 |
| 6 | $C_2H_5$ | n-$C_3H_7$ | O | O | $N(CH_3)_2$ | yellow oil | 1.5621 |
| 7 | $C_2H_5$ | n-$C_3H_7$ | S | O | $N(CH_3)_2$ | yellow oil | 1.5868 |
| 8 | $C_2H_5$ | n-$C_3H_7$ | O | S | $N(CH_3)_2$ | yellow oil | 1.5984 |
| 9 | $C_2H_5$ | n-$C_3H_7$ | S | S | $N(CH_3)_2$ | yellow oil | 1.6221 |
| 10 | $C_2H_5$ | n-$C_3H_7$ | S | O | $NHC_4H_9$—s | yellow oil | 1.5670 |
| 11 | $C_2H_5$ | n-$C_3H_7$ | O | S | $NHC_4H_9$—s | yellowish brown oil | 1.5660 |
| 12 | $C_2H_5$ | n-$C_3H_7$ | S | S | $NHC_4H_9$—s | pale yellow oil | 1.5887 |
| 13 | $C_2H_5$ | n-$C_3H_7$ | O | O | $C_4H_9$—s / N\COCH_3 | yellowish brown oil | 1.5269 |

TABLE 2

Formula

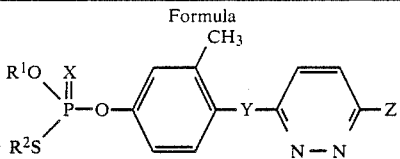

| Compound No. | $R^1$ | $R^2$ | X | Y | Z | Appearance | $n_D^{25}$ |
|---|---|---|---|---|---|---|---|
| 14 | $CH_3$ | s-$C_4H_9$ | O | O | Cl | pale yellow oil | 1.5493 |

TABLE 2-continued

Formula

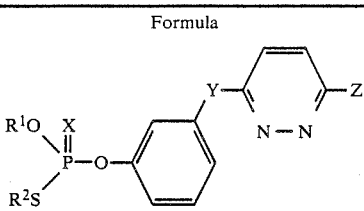

| Compound No. | $R^1$ | $R^2$ | X | Y | Z | Appearance | $n_D^{25}$ |
|---|---|---|---|---|---|---|---|
| 15 | $C_2H_5$ | n-$C_3H_7$ | O | O | Cl | colorless oil | 1.5522 |
| 16 | $C_2H_5$ | n-$C_3H_7$ | S | O | Cl | colorless oil | 1.5761 |

TABLE 3

Formula

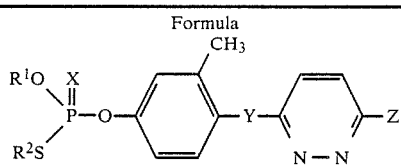

| Compound No. | $R^1$ | $R^2$ | X | Y | Z | Appearance | $n_D^{25}$ |
|---|---|---|---|---|---|---|---|
| 17 | $C_2H_5$ | n-$C_3H_7$ | O | O | H | pale yellow oil | 1.5514 |
| 18 | $C_2H_5$ | n-$C_3H_7$ | O | O | Cl | colorless oil | 1.5569 |
| 19 | $C_2H_5$ | n-$C_3H_7$ | O | S | Cl | pale yellow oil | 1.5786 |
| 20 | $C_2H_5$ | n-$C_3H_7$ | S | S | Cl | pale yellow oil | 1.6119 |
| 21 | $C_2H_5$ | n-$C_3H_7$ | O | O | $N(CH_3)_2$ | yellow oil | 1.5641 |
| 22 | $C_2H_5$ | n-$C_3H_7$ | O | O | $NHC_4H_9$—s | pale yellow oil | 1.5453 |

TABLE 4

Formula

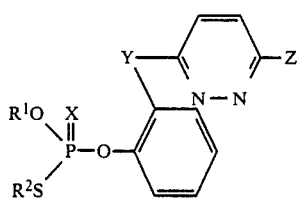

| Compound No. | $R^1$ | $R^2$ | X | Y | Z | Appearance | $n_D^{25}$ or (m.p.) |
|---|---|---|---|---|---|---|---|
| 23 | $CH_3$ | $s\text{-}C_4H_9$ | O | O | Br | colorless oil | 1.5594 |
| 24 | $C_2H_5$ | $n\text{-}C_3H_7$ | O | O | Br | colorless oil | 1.5654 |
| 25 | $C_2H_5$ | $n\text{-}C_3H_7$ | S | O | Br | pale yellow crystal | (72–74° C.) |
| 26 | $C_2H_5$ | $n\text{-}C_3H_7$ | O | S | Br | colorless oil | 1.5938 |
| 27 | $CH_3$ | $s\text{-}C_4H_9$ | O | O | Cl | pale yellow oil | 1.5539 |
| 28 | $CH_3$ | $s\text{-}C_4H_9$ | O | S | Cl | colorless oil | 1.5849 |
| 29 | $C_2H_5$ | $n\text{-}C_3H_7$ | O | O | Cl | colorless oil | 1.5545 |
| 30 | $C_2H_5$ | $n\text{-}C_3H_7$ | S | O | Cl | colorless crystal | (66–67.5° C.) |
| 31 | $C_2H_5$ | $n\text{-}C_3H_7$ | O | S | Cl | colorless oil | 1.5808 |
| 32 | $C_2H_5$ | $n\text{-}C_3H_7$ | S | S | Cl | pale yellow oil | 1.6139 |
| 33 | $C_2H_5$ | $i\text{-}C_8H_7$ | O | O | Cl | pale yellow crystal | (65.5–68.0° C.) |
| 34 | $C_2H_5$ | $n\text{-}C_4H_9$ | O | O | Cl | colorless oil | 1.5462 |
| 35 | $C_2H_5$ | $i\text{-}C_4H_9$ | O | O | Cl | colorless crystal | (44.5–47.0° C.) |
| 36 | $C_2H_5$ | $s\text{-}C_4H_9$ | O | O | Cl | colorless crystal | (63.0–66.0° C.) |
| 37 | $C_2H_5$ | $n\text{-}C_3H_7$ | O | O | $CH_3$ | colorless oil | 1.5463 |
| 38 | $C_2H_5$ | $n\text{-}C_3H_7$ | S | O | $CH_3$ | pale yellow crystal | (46–48° C.) |
| 39 | $C_2H_5$ | $n\text{-}C_3H_7$ | O | O | $OCH_3$ | colorless oil | 1.5372 |
| 40 | $C_2H_5$ | $n\text{-}C_3H_7$ | S | O | $OCH_3$ | colorless crystal | (51–52.5° C.) |
| 41 | $C_2H_5$ | $n\text{-}C_3H_7$ | O | O | $SC_2H_5$ | colorless crystal | (44–46° C.) |
| 42 | $C_2H_5$ | $n\text{-}C_3H_7$ | S | O | $SC_2H_5$ | colorless crystall | (72–74.5° C.) |
| 43 | $C_2H_5$ | $n\text{-}C_3H_7$ | O | O | $NH_2$ | yellow oil | 1.5480 |
| 44 | $C_2H_5$ | $n\text{-}C_3H_7$ | S | O | $NH_2$ | pale yellow oil | 1.5721 |
| 45 | $C_2H_5$ | $n\text{-}C_3H_7$ | O | S | $N(CH_3)_2$ | pale yellow oil | 1.5951 |
| 46 | $C_2H_5$ | $n\text{-}C_3H_7$ | S | S | $NHC_4H_9\text{—}s$ | pale yellow crystal | (70–72.5° C.) |

EXAMPLE 6

O-Ethyl-S-n-propyl-O-[2-(3-methoxypyridazinyl-6-oxy)phenyl]phosphorothioate (Compound No. 39)

0.5 g of sodium are dissolved in 50 ml of ethyl alcohol, followed by introducing hydrogen sulfide gas for 15 minutes. Then dried nitrogen gas is introduced into the mixture to repel the execess of hydrogen sulfide gas. To the mixture are added 7.4 g of O,O-diethyl-O-[2-(3-methoxypyridazinyl-6-oxy)phenyl]phosphorothioate and the mixture is refluxed for 3 hours. Then the mixture is concentrated under reduced pressure to remove ethyl alcohol. The residue is suspended in 80 ml of acetone, followed by adding 2.5 g of n-propyl bromide. The mixture is refluxed for 15 hours, and concentrated under reduced pressure to remove acetone. To the residue is added toluene and the resulting solution is washed with water and dryed over magnesium sulfate. Evaporation of toluene gives an oily product which is purified on a column of silica gel (eluent: n-hexane:acetone=4:1) to yield 1.9 g of an oily title compound.

$n_D^{25}$ 1.5372.

EXAMPLE 7

O-Ethyl-S-n-propyl-O-[2-(3-chloropyridazinyl-6-oxy)-phenyl]phosphorothioate (Compound No. 29)

To 80 ml of acetonitrile are dissolved 4.4 g of 3-chloro-6-(2-hydroxyphenoxy)pyridazine and 3.9 g of S-n-propyl phosphorodichloridothioate, followed by adding 2.4 g of γ-collidine dropwise. The mixture is stirred at room temperature for 4 hours. Then, to the mixture are added 1.0 g of ethyl alcohol and 2.4 g of γ-collidine.

After stirring at 50° C. for 3 hours, the mixture is concentrated under reduced pressure to remove acetonitrile. To the residue is added toluene, washed with water, diluted hydrochloric acid and water in that order. The mixture is dryed over magnesium sulfate and concentrated under reduced pressure to give an oily product which is purified on a column of silica gel (eluent: n-hexane:acetone=4:1) to yield 2.7 g of an oily title compound.

$n_D^{25}$ 1.5545.

EXAMPLE 8

Emulsifiable Concentrate

| | |
|---|---|
| Compound No. 30 | 20 wt. % |
| Xylene | 75 wt. % |
| Polyoxyethylene glycol ether (Nonipol 85 ®) | 5 wt. % |

The above components are admixed to pepare an emulsifiable concentrate (applied after the properly diluting it with water).

EXAMPLE 9

Wettable Powder

| | |
|---|---|
| Compound No. 40 | 30 wt. % |
| Sodium ligninesulfonate | 5 wt. % |
| Polyoxyethylene glycol ether (Nonipol 85 ®) | 5 wt. % |
| White carbon | 30 wt. % |
| Clay | 30 wt. % |

The above components are admixed to prepare a wettable powder (applied after the properly diluting it with water).

EXAMPLE 10

Dust

| Compound No. 30 | 3 wt. % |
|---|---|
| White carbon | 3 wt. % |
| Clay | 94 wt. % |

The above components are admixed to prepare a dust.

EXAMPLE 11

Granules

| Compound No. 39 | 10 wt. % |
|---|---|
| Sodium ligninsulfonate | 5 wt. % |
| Clay | 85 wt. % |

The above components are admixed to prepare granules.

REFERENCE EXAMPLE 1

3-Chloro-6-(2-hydroxyphenoxy)pyridazine (Compound No. A)

14.9 g of 3,6-dichloropyridazine and 14.3 g of catechol are dissolved in 40 ml of dimethyl sulfoxide, followed by addition of 15.2 g of anhydrous potassium carbonate. The mixture is heated gradually, and stirred at 80° to 90° C. for 2 hours. The reaction mixture, after cooling down, is poured into 300 ml of a 10% aqueous solution of sodium hydroxide. The resulting insoluble precipitates are filtered off and the filtrate is neutralized with concentrated hydrochloric acid. After the resulting crystals are filtrated, followed by drying to yield 13.4 g of title compound. When this product is subjected to treatment with activated charcoal and recrystallized from acetone, to yield colorless crystals of the title compound melting at 146.5°–148° C.

REFERENCE EXAMPLE 2

3-(3-Hydroxyphenoxy)pyridazine (Compound No. E)

11.1 g of 3-chloro-6-(3-hydroxyphenoxy)pyridazine are dissolved in 100 ml of ethanol, followed by addition of 6 ml of concentrated ammonia water and 1.0 of 5% Pd-C. Then catalytic reduction is carried out at 50° C. under atmospheric pressure. The theroretical amount of hydrogen gas is almost completely absorbed in about 1 hour. The reaction mixture is filtered and the filtrate is concentrated to dryness.

The residue is subjected to extraction with acetone, and the acetone is then evaporated off under reduced pressure to yield 8.3 g of title compound. This product is recrystallized from methanol to yield colorless crystals of the title compound melting at 107°–109.5° C.

REFERENCE EXAMPLE 3

3-Chloro-6-(4-hydroxyphenylthio)pyridazine (Compound No. K)

A mixture of 14.9 g of 3,6-dichloropyridazine, 13.9 g of thiohydroquinone and 15.2 g of anhydrous potassium carbonate in 50 ml of dimethylacetamide, is heated gradually, and stirred at 80° C. for 2 hours.

The reaction mixture, after cooling down, is poured into 400 ml of a 10% aqueous solution of sodium hydroxide and the insoluble precipitates are filtered off. The filtrate is neutralized with concentrated hydrochloric acid, the resulting separated oily substance is extracted with methyl isobutyl ketone. The extractant is evaporated off under reduced pressure to yield a brown oily substance. This product is purified by column chromatography (silica gel: Wakogel C-200 ® produced by Wako Pure Chemical Co.; eluent: hexane/acetone=3/1 v/v) to yield 13.1 g of colorless crystals of the title compound melting at 162°–163° C.

REFERENCE EXAMPLE 4

3-Dimethylamino-6-(2-hydroxyphenylthio)pyridazine (Compound No. C)

A mixture of 15.8 g of 3-chloro-6-dimethylaminopyridazine, 12.6 g of thiocatechol and 13.8 g of anhydrous potassium carbonate in 50 ml of dimethylacetamide is stirred at 130°–140° C. for 3 hours.

The resulting mixture is treated in the same manner as Example 1 to yield 21.8 g of title compound. This product is recrystallized from acetone to yield colorless crystals of the title compound melting at 89°–92° C.

REFERENCE EXAMPLE 5

3-Chloro-6-(3-hydroxyphenylthio)pyridazine (Compound No. G)

A mixture of 14.9 g of 3,6-dichloropyridazine, 13.9 g of thioresorchinol, and 15.2 g of anhydrous potassium carbonate in 50 ml of dimethylacetamide are strirred at 60°–70° C. for 2 hours.

The resulting mixture is treated by the same manner as Example 1 to yield 19.1 g of title compound. Recrystallization from acetone gives colorless crystals of the title compound melting at 170°–173° C.

The compounds which is produced in the same manner as Reference Examples 1 to 5 are listed in Table 5, inclusive of the compounds obtained in Reference Examples 1 to 5.

TABLE 5

| Compound No. | Compound | Appearance | m.p. (°C.) |
|---|---|---|---|
| A | 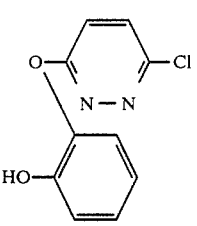 | colorless crystal | 146.5–148 |

TABLE 5-continued

| Compound No. | Compound | Appearance | m.p. (°C.) |
|---|---|---|---|
| B | 3-chloro-6-(2-hydroxyphenylazo)thio-pyridazine | colorless crystal | 145.5–147 |
| C | 3-dimethylamino-6-(2-hydroxyphenylazo)thio-pyridazine | colorless crystal | 89–92 |
| D | 3-(sec-butylamino)-6-(2-hydroxyphenylazo)thio-pyridazine | colorless crystal | 138.5–140 |
| E | 3-(3-hydroxyphenoxy)pyridazine | colorless crystal | 107–109.5 |
| F | 3-chloro-6-(3-hydroxyphenoxy)pyridazine | colorless crystal | 182–184 |
| G | 3-chloro-6-(3-hydroxyphenylthio)pyridazine | colorless crystal | 170–173 |
| H | 3-dimethylamino-6-(3-hydroxyphenoxy)pyridazine | colorless crystal | 149–150.5 |
| I | 3-(4-hydroxyphenoxy)pyridazine | colorless crystal | 170–172 |

TABLE 5-continued
| Compound No. | Compound | Appearance | m.p. (°C.) |
|---|---|---|---|
| J | 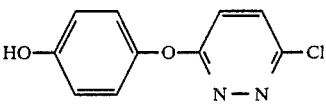 | colorless crystal | 190–191 |
| K | 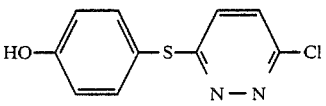 | colorless crystal | 162–163 |
| L | 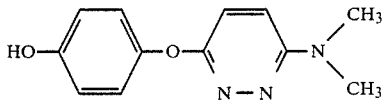 | colorless crystal | 190–192 |
| M | 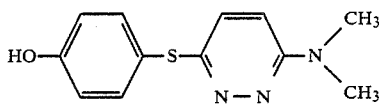 | colorless crystal | 159–161 |
| N | 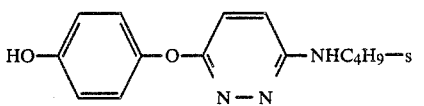 | colorless crystal | 54–56 |
| O | 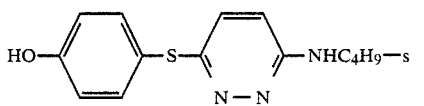 | yellow viscous oil | — |
| P | 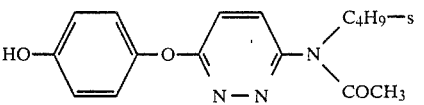 | yellowish brown viscous oil | — |
| Q | 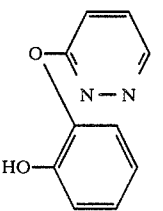 | colorless crystal | 159–160 |
| R | 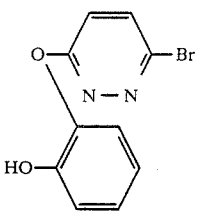 | colorless crystal | 146.5–147.5 |
| S | 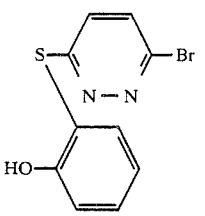 | colorless crystal | 155–156 |

TABLE 5-continued

| Compound No. | Compound | Appearance | m.p. (°C.) |
|---|---|---|---|
| T | (structure) | colorless crystal | 136–137.5 |
| U | (structure) | colorless crystal | 152–155 |
| V | (structure) | colorless crystal | 117–118.5 |
| W | (structure) | colorless crystal | 122–124 |

TEST EXAMPLE 1

Effectiveness of *Spondoptera litura*

Each of the test compounds listed in the following table is processed into an emulsifiable concentrate in accordance with the formulation of Example 6. The emulsifiable concentrate is diluted with water (Dyne ®, a spreading agent produced by Takeda Chemical Ind. Ltd., as diluted 3,000-fold) to prepare a 100 ppm aqueous solution.

Using a spray gun (nozzle pressure of 1 kg/cm² gauge), 20 ml of the aqueous 100 ppm solution is sprayed over soybean seedlings in a spraying chamber (on 10th day after germination) which have been raised in jiffy pots (6 cm in diameter). Two main leaves are respectively cut off from the seedlings 2 hours and 6 days after the spraying. Each of the leaves is put into an ice cream cup (diameter: 6 cm, depth: 4 cm), and 10 larvae of *Spodoptera litura* at the 3rd instar are put into each of the cups. The cups are left in a room at 25° C.; after 48 hours, dead larvae are counted. The test is repeated two times. The results are shown in terms of mortality (%) in Table 6.

$$\text{Mortality (\%)} = \frac{\text{Number of dead larvae}}{\text{Number of released larvae}} \times 100$$

The following compounds are used for controls.
(A) Prothiophos:

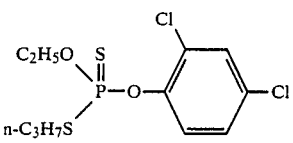

(trade name: Tokuthion)
(B) Fenitrothion:

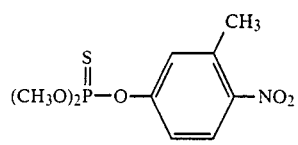

(trade name: Sumithion

The same compounds are used for controls also in the following Test Examples.

TABLE 6

| Test Compound (Compound No.) | Mortality | |
|---|---|---|
| | 2 hours after spraying | 6th day after spraying |
| 1 | 100 | 90 |
| 2 | 100 | 100 |
| 3 | 100 | 90 |
| 4 | 100 | 95 |
| 6 | 100 | 90 |
| 15 | 100 | 100 |

TABLE 6-continued

| Test Compound (Compound No.) | Mortality | |
|---|---|---|
| | 2 hours after spraying | 6th day after spraying |
| 16 | 100 | 100 |
| 17 | 100 | 100 |
| 18 | 100 | 100 |
| 19 | 100 | 90 |
| 20 | 100 | 90 |
| 21 | 100 | 100 |
| 22 | 100 | 100 |
| 24 | 100 | 100 |
| 25 | 100 | 100 |
| 26 | 100 | 95 |
| 27 | 100 | 100 |
| 28 | 100 | 95 |
| 27 | 100 | 90 |
| 30 | 100 | 100 |
| 36 | 100 | 100 |
| 38 | 100 | 100 |
| 39 | 100 | 100 |
| 40 | 100 | 100 |
| 41 | 100 | 100 |
| 42 | 100 | 100 |
| (Control) | 100 | 10 |
| Prothiohos | 80 | 0 |
| Fenitrothion | | |
| Untreated control | 0 | 0 |

TEST EXAMPLE 2

Effectiveness on *Tetranychus urticae*

Each of the compounds listed in the following table is processed into an emulsifiable concentrate in accordance with the formulation of Example 6. The emulsifiable concentrate is diluted with water (Dyne®, a spreading agent produced by Takeda Chemical Ind. Ltd., as diluted 3,000-fold) to prepare a 500 ppm aqueous solution. Ten female adult of *Tetranychus urticae* are put into each kidney been seedling raised in a jiffy pot (6 cm in diameter), and left in a glass house at 28° C. for 24 hours. Each pot is taken out of the glass house; 20 ml of the aqueous solution as prepared above is spread over each kidney bean seedling. The jiffy pots are laid in the glass house again. Larvae and adult which are alive on the leaves are counted at the 2nd and 7th days after the spreading treatment. The test is repeated two times. The results are shown in rating of effects in Table 7. The degrees are determined on the basis of percent decrease.

Percent decrease =

$$\frac{\text{test mites} - \text{adults at each observation day}}{\text{Number of test mites}} \times 100$$

| Rating of effects | Percent decrease (%) |
|---|---|
| 0 | ≦20 |
| 1 | 21–50 |
| 2 | 51–89 |
| 3 | ≧90 |

TABLE 7

| Test Compound (Compound No.) | Rating of effect | |
|---|---|---|
| | Day-2 | Day-7 |
| 1 | 3 | 3 |
| 2 | 3 | 3 |
| 3 | 3 | 3 |
| 4 | 3 | 3 |
| 5 | 3 | 3 |

TABLE 7-continued

| Test Compound (Compound No.) | Rating of effect | |
|---|---|---|
| | Day-2 | Day-7 |
| 8 | 3 | 3 |
| 9 | 3 | 3 |
| 13 | 3 | 3 |
| 14 | 3 | 3 |
| 15 | 3 | 3 |
| 16 | 3 | 3 |
| 17 | 3 | 3 |
| 18 | 3 | 3 |
| 19 | 3 | 3 |
| 20 | 3 | 3 |
| 21 | 3 | 3 |
| 24 | 3 | 3 |
| 25 | 3 | 3 |
| 26 | 3 | 3 |
| 27 | 3 | 3 |
| 28 | 3 | 3 |
| 29 | 3 | 3 |
| 30 | 3 | 3 |
| 31 | 3 | 3 |
| 32 | 3 | 3 |
| 37 | 3 | 3 |
| 38 | 3 | 3 |
| 39 | 3 | 3 |
| 40 | 3 | 3 |
| 41 | 3 | 3 |
| 42 | 3 | 3 |
| 43 | 3 | 3 |
| 44 | 3 | 3 |
| 45 | 3 | 3 |
| 46 | 3 | 3 |
| (Control) | 3 | 0 |
| Prothiophos | 3 | 0 |
| Fenitrothion | | |
| Untreated control | 0 | 0 |

TEST EXAMPLE 3

Toxicological Test

The oral acute toxicity values obtained with five-week aged, ddY-SLC strained male mice are shown in Table 8.

TABLE 8

| Compound No. | LD$_{50}$ (mg/kg) | Compound No. | LD$_{50}$ (mg/kg) |
|---|---|---|---|
| 3 | about 300 | 25 | >300 |
| 4 | >300 | 26 | about 300 |
| 5 | >300 | 30 | >300 |
| 7 | >300 | 31 | >300 |
| 8 | about 300 | 32 | >300 |
| 9 | >300 | 33 | >300 |
| 10 | >300 | 38 | >300 |
| 11 | >300 | 39 | about 300 |
| 12 | >300 | 40 | >300 |
| 16 | >300 | 41 | about 300 |
| 18 | >300 | 42 | >300 |
| 19 | >300 | 44 | >300 |
| 20 | >300 | 46 | >300 |
| 24 | about 300 | | |

What is claimed is:

1. A compound of the formula:

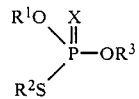

wherein $R^1$ and $R^2$ are respectively a straight or branched chain alkyl group of 1 to 6 carbon atoms; $R^3$ is a group of the formula:

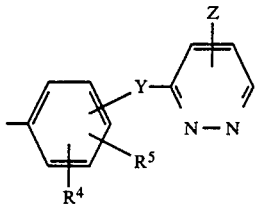

wherein $R^4$ and $R^5$ are respectively a hydrogen atom or a straight or branched chain alkyl group of 1 to 6 carbon atoms, and Z is a hydrogen atom, a halogen atom, a straight or branched chain alkyl group of 1 to 6 carbon atoms, a straight or branched chain alkoxy group of 1 to 6 carbon atoms, a straight or branched chain alkylthio group of 1 to 6 carbon atoms, or a group of the formula:

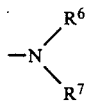

in which $R^6$ and $R^7$ are respectively a hydrogen atom, a straight or branched chain alkyl group of 1 to 6 carbon atoms or a carboxylic acyl group, and Y is an oxygen or sulfur atom; and X is an oxygen or sulfur atom, or salt thereof.

2. The compound as claimed in claim 1, wherein $R^3$ is a group of the formula:

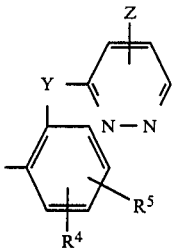

wherein the symbols have the same meanings as defined in claim 1.

3. The compound as claimed in claim 1, wherein Y is an oxygen atom.

4. The compound as claimed in claim 1, wherein $R^4$ is a hydrogen atom; and $R^5$ is a hydrogen atom or a straight or branched chain alkyl group of 1 to 6 carbon atoms.

5. The compound as claimed in claim 1, wherein Z is a hydrogen atom, a halogen atom, a straight or branched chain alkyl group of 1 to 6 carbon atoms or a straight or branched chain alkoxy group of 1 to 6 carbon atoms.

6. The compound as claimed in claim 1, wherein $R^4$ and $R^5$ are respectively a hydrogen atom.

7. The compound as claimed in claim 1, namely O-ethyl-S-n-propyl-O-[2-(3-chloropyridazinyl-6-oxy)-phenyl]phosphorothiolothionate.

8. The compound as claimed in claim 1, namely O-ehtyl-S-n-propyl-O-[2-(3-methoxypyridazinyl-6-oxy)-phenyl]phosphorothiolothionate.

9. The compound as claimed in claim 1, namely O-ethyl-S-n-propyl-O-[2-(3-methoxypyridazinyl-6-oxy)-phenyl]phosphorothiolate.

10. The compound as claimed in claim 1, wherein the acyl carboxylic group is an aliphatic acyl group of 1 to 6 carbon atoms.

11. The compound as claimed in claim 1, wherein Y is oxygen; $R^4$ and $R^5$ are respectively hydrogen; and Z is hydrogen, a halogen or a straight or branched chain alkoxy group of 1 to 6 carbon atoms.

12. An insecticidal-acaricidal composition which comprises an insecticidally-acaricidally effective amount of the compound or salt thereof as defined in claim 1 and an inert carrier therefor.

* * * * *